United States Patent
Job

(10) Patent No.: US 12,239,435 B2
(45) Date of Patent: Mar. 4, 2025

(54) METHOD AND SYSTEM FOR DETERMINING AT LEAST ONE PRODUCTION VALUE FOR PRODUCING A CUSTOM-TAILORED COMPRESSION GARMENT FOR A LIMB AND COMPUTER PROGRAM

(71) Applicant: MEDI GMBH & CO. KG, Bayreuth (DE)

(72) Inventor: Jutta Job, Harsdorf (DE)

(73) Assignee: MEDI GMBH & CO. KG, Bayreuth (DE)

( * ) Notice: Subject to any disclaimer, the term of this patent is extended or adjusted under 35 U.S.C. 154(b) by 631 days.

(21) Appl. No.: 17/601,036

(22) PCT Filed: Feb. 18, 2020

(86) PCT No.: PCT/EP2020/054174
§ 371 (c)(1),
(2) Date: Oct. 1, 2021

(87) PCT Pub. No.: WO2020/200576
PCT Pub. Date: Oct. 8, 2020

(65) Prior Publication Data
US 2022/0167874 A1    Jun. 2, 2022

(30) Foreign Application Priority Data
Apr. 3, 2019 (EP) .................... 19167008

(51) Int. Cl.
*A61B 5/107* (2006.01)
*A61B 5/00* (2006.01)
(Continued)

(52) U.S. Cl.
CPC .......... *A61B 5/1079* (2013.01); *A61B 5/0064* (2013.01); *A61B 5/1072* (2013.01);
(Continued)

(58) Field of Classification Search
CPC ... A61B 5/1079; A61B 5/0064; A61B 5/1072; A61B 5/6898; A61B 5/7267;
(Continued)

(56) References Cited

U.S. PATENT DOCUMENTS

2016/0235354 A1 * 8/2016 Weiler ................ A61B 5/4878
2018/0042322 A1 * 2/2018 Weiler ................... A41H 3/007
(Continued)

FOREIGN PATENT DOCUMENTS

DE      102016118073 A1      3/2018

OTHER PUBLICATIONS

Kowalski, Krzysztof et al, "Influence of a Compression Garment on Average and Local Changes in Unit Pressure", Fibres and Textiles in Eastern Europe, vol. 25, No. 0, Dec. 31, 2017, pp. 68-74.
(Continued)

*Primary Examiner* — Sanjay Cattungal
(74) *Attorney, Agent, or Firm* — Rimon PC

(57) ABSTRACT

Computer-implemented method for determining at least one production value for producing a custom tailored compression garment for a limb involving receiving a three dimensional dataset of the limb, evaluating the dataset to derive at least one reference information describing the position of an anatomical feature of the limb, determining the at least one measurement position for the at least one production value in the three dimensional dataset using at least one rule of a rule set, and determining the at least one production value from the three dimensional dataset at the at least one determined measurement position.

13 Claims, 2 Drawing Sheets

Figure 1:
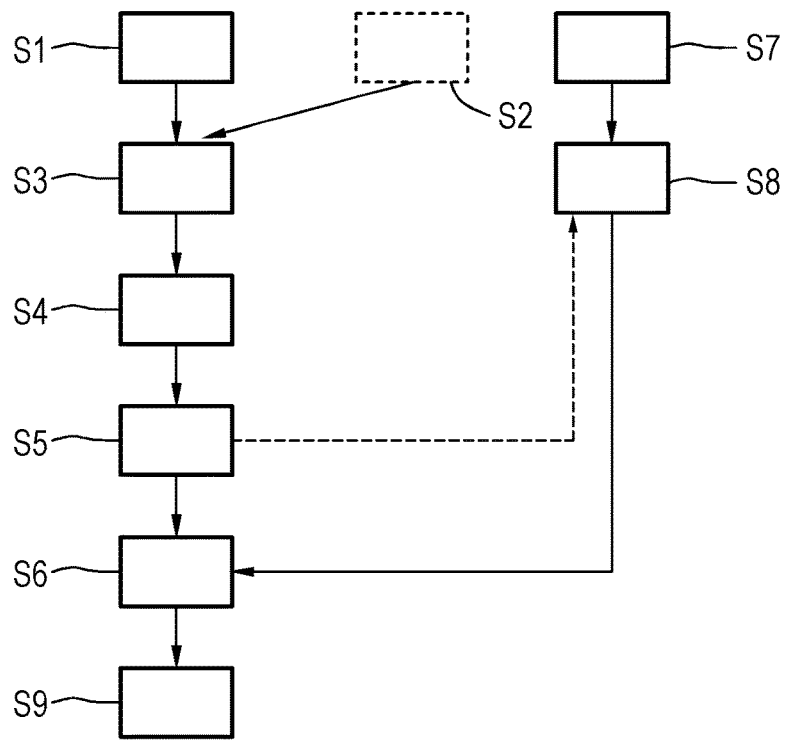

(51) Int. Cl.
*A61F 13/08* (2006.01)
*D04B 1/26* (2006.01)
*D04B 9/52* (2006.01)
*G06N 3/02* (2006.01)

(52) U.S. Cl.
CPC ............ *A61B 5/6898* (2013.01); *A61F 13/08* (2013.01); *D04B 1/265* (2013.01); *D04B 9/52* (2013.01); *G06N 3/02* (2013.01)

(58) Field of Classification Search
CPC ..... A61B 5/7264; A61B 5/0022; A61F 13/08; D04B 1/265; D04B 9/52; D04B 37/02; G06N 3/02; G16H 20/40; G16H 50/50
See application file for complete search history.

(56) References Cited

U.S. PATENT DOCUMENTS

| | | | |
|---|---|---|---|
| 2018/0168261 A1* | 6/2018 | Weiler | A41H 3/04 |
| 2019/0208850 A1* | 7/2019 | Weiler | G16H 50/50 |
| 2021/0274874 A1* | 9/2021 | Atmanspacher | D04B 1/265 |
| 2021/0298401 A1* | 9/2021 | Thelemann | A41H 1/02 |
| 2022/0338586 A1* | 10/2022 | Waldie | A41H 3/04 |

OTHER PUBLICATIONS

Liu, Rong et al, "Determination of leg cross-sectional curvatures and application in pressure prediction for lower body compression garments", Textile Research Journal, vol. 89, No. 10, Jun. 11, 2018, pp. 1835-1852.

* cited by examiner

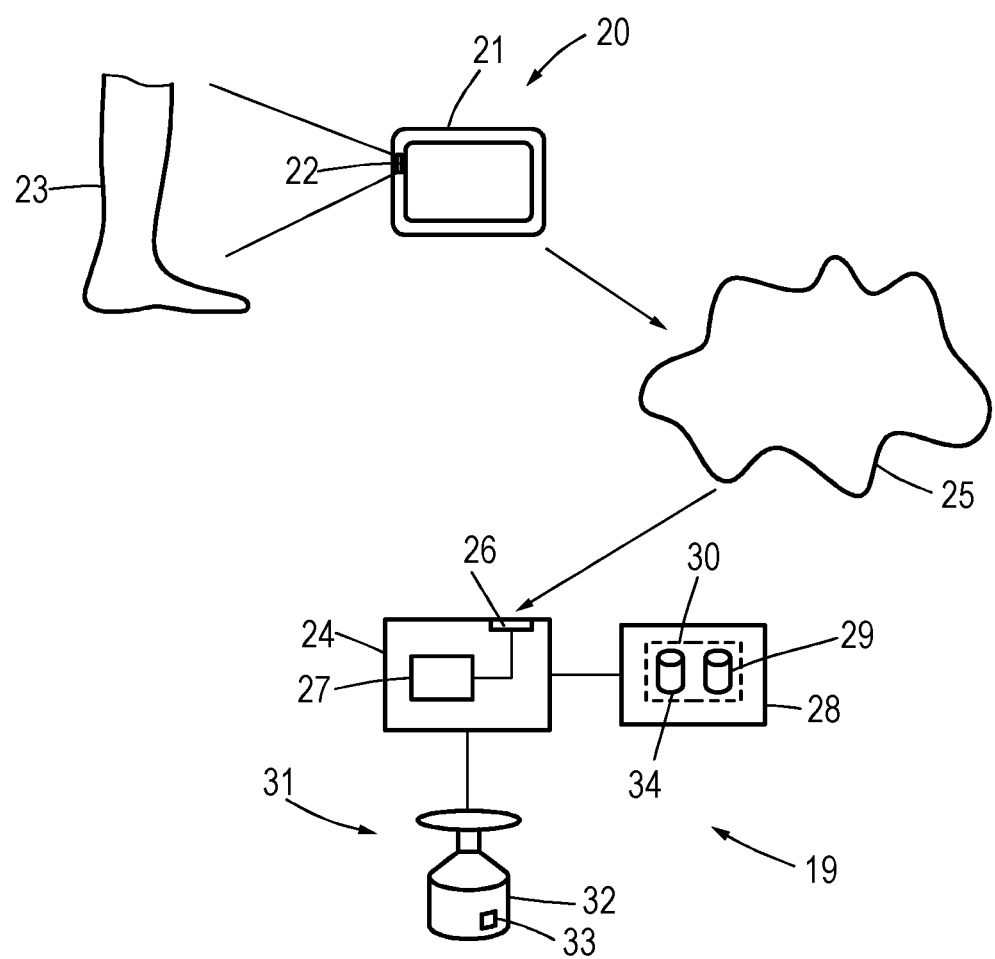

METHOD AND SYSTEM FOR DETERMINING AT LEAST ONE PRODUCTION VALUE FOR PRODUCING A CUSTOM-TAILORED COMPRESSION GARMENT FOR A LIMB AND COMPUTER PROGRAM

CROSS-REFERENCE TO RELATED APPLICATIONS

This application claims priority to Patent Cooperation Treaty application serial number PCT/EP2020/054174, filed Feb. 18, 2020, which claims priority to European patent application serial number 19167008.2, filed Apr. 3, 2019, the contents of each of which are incorporated herein by reference in their entirety.

The invention concerns a computer-implemented method and a system for determining at least one production value for producing a custom-tailored compression garment for a limb, wherein the production value is associated with at least one measurement position along the length of the limb. The invention further concerns a method for producing a compression garment for a limb of a patient and a computer program.

Compression garments have already been proposed in the state of the art and exist in a wide variety of embodiments and for various applications. Compression garments are used to apply a desired compression to a limb of a garment, in particular for therapeutic reasons. Known compression garments comprise compression wraps, compression stockings, compression bandages and the like. As the properties of the limbs of persons usually differ from each other, to achieve the desired therapeutic effect, it is known to produce these compression garments custom-tailored for a certain person, for example a patient. In particular, measurements may be performed at the limb of the patient to obtain measurement values, which can be used for production of a customized compression garment for the person.

In known approaches, at different measurement positions along the limb, a so-called skin value (or "skin measure") and so-called tension value (or "tension measure"/"tight tape measure"), which, in German, are called "Hautmaß" and "Zugmaß", are measured, for example by staff of a medical store. The measurement positions along the length of the limb are also chosen by the staff, for example using guidelines like RAL-GZ 387/1. Measurement using tension and/or no tension is, for example, described in Anett Reißhauer et al., "Kompendium der lymphologischen Kompressionsversorgung", Bundesfachschule für Orthopädie-Technik, ISBN: 978-3-00-024717-0.

The skin value is the circumference of the limb at the skin surface without applying pressure onto the human tissue, associated with and taken at a measurement position usually chosen by the staff according to guidelines and experience. The tension value, describing the circumference under the compression to be applied by the garment, is usually determined at the same measurement position under tension of the measuring tape, that is, the measuring tape is pulled tight and applies pressure onto the tissue which should at least essentially resemble the compression to be applied by the compression garment. That is, both the measurement positions and the tension value are heavily dependent on the skill level, sensitivity and experience of the person performing the measurement. While the skin value may, for example, also be determined by other means, for example imaging or scanning devices, the measurement positions and the tension value can, to date, only be determined by manual choice or measurement using a certain tension, respectively, such that the quality and reliability of the measurement positions and tension value rests in the hands of the staff of medical stores.

However, finding the right and suitable measurement positions along the length of the limb is important for producing a fitting custom-tailored compression garment of a high quality, since, for example, knitting parameters for an automatic knitting machine are determined depending on production values, like skin value and tension value, expected to be measured at the respective measurement positions. Additionally, production values may also comprise length values which may depend on measurement positions or at least reference positions of anatomical features determined manually along the limb.

An additionally known production value is, for example, the table value (or "table measure"), that is, the circumference of the compression garment while not donned.

In summary, measurement positions for measuring certain production values are usually chosen by the person performing the measurements. This choice is mainly dependent on the know-how/experience of the person performing the measurement. In consequence, faulty measurements are common such that the persons for whom garments are produced often file complaints. Additionally, staff of medical stores is often overchallenged.

It is thus an object of the current invention to provide a possibility to simplify the measurement process regarding custom-tailored garments and/or to simplify and standardize the choice of measurement positions.

This object is achieved by providing the methods, determination system and computer program according to the independent claims. Advantageous embodiments are described in the dependent claims.

A computer-implemented method as initially described, according to the invention, comprises the following steps:
  receiving a three-dimensional dataset of the limb acquired using a 3D scan device,
  evaluating the three-dimensional dataset to derive at least one reference information describing the position of an anatomical feature of the limb along the length of the limb,
  determining the at least one measurement position for the at least one production value in the three-dimensional dataset using at least one rule of a rule set, wherein each rule relates at least one reference information to at least one measurement position,
  determining the at least one production value from the three-dimensional dataset at the at least one determined measurement position.

The invention thus allows a completely automated determination of production values for a custom-tailored compression garment by using and evaluating a three-dimensional dataset of the limb of the person, in particular a patient. 3D scan devices able to scan limbs, in particular a leg of a person, have already been proposed in the state of the art and may, for example, use imaging techniques. The resulting three-dimensional dataset should at least describe the surface of the limb, that is, its outline, but can also provide additional relevant information. According to the invention, the three-dimensional dataset is evaluated to derive reference information regarding anatomical features of the limb, in particular their position along the length of the limb. Such anatomical features may, in particular, be anatomical landmarks, but the definition of other anatomical features also lies within the scope of the current invention. Evaluation algorithms that may be used to detect and localize anatomical features are, in principle, in particular from diagnostic applications, already known in the state of the art and may comprise segmentation, pattern recognition, comparisons and/or registrations to data of an anatomical atlas, and even machine learning approaches.

Compression garments are usually produced and worn to fulfil a certain function regarding the limb and, thus, its anatomical features. To produce a custom-tailored compression garment optimally fulfilling its function, it is thus expedient to provide production information, that is, production values, at relevant measurement positions. In other words, it is advantageous to define and choose measurement positions in certain physical and/or anatomical relationships to anatomical features. These relationships, in the current invention, are implemented by using a rule set comprising rules which relate reference information to measurement positions. A rule of the rule set describes how a measurement position may be derived from reference information obtained by evaluating the three-dimensional dataset. For example, a position of an anatomical feature described by reference information may, in some cases, already define at least one measurement position, while, regarding other measurement positions, physical and/or anatomical considerations may lead to more complex relationships, for example certain offsets to at least one position of an anatomical feature, relative positions regarding anatomical features or even calculation instructions. It is noted that rules may also comprise decision trees, for example choosing measurement positions differently depending on actual reference information for the limb.

Once the measurement positions along the limb have been determined, the production values may also be automatically determined from the three-dimensional dataset. As the measurement positions are also determined from the three-dimensional dataset, it is of course conceivable that measurement positions themselves are used for calculation of the production value, in particular regarding length values, as further discussed below, or even as production values. Production values in the sense of the current invention may comprise manufacturing values, for example directly usable as control parameters in a knitting machine or the like, and/or garment values describing properties, in particular dimensions, of the garment, and/or intermediate values. The latter, which are preferably determined in the method according to the invention, are, for example, used to derive a corresponding knitting program for a knitting machine therefrom, like the already mentioned skin values and tension values.

The invention provides the possibility of fully automating the determination of production values, without risking a false definition of measurement positions, since a three-dimensional dataset of the limb acquired from the person, by, in particular, contact-free measurement, is used and evaluated, applying a physically motivated rule set. As will be discussed in detail further below, the method may advantageously be combined with approaches for determining production values not directly derivable from the three-dimensional dataset, for example the tension value, fully automatically from input information, in particular comprising other production values derivable from the three-dimensional dataset.

Preferably, the three-dimensional dataset may be acquired using a contact-free, imaging-based 3D scan device, in particular a tablet or mobile phone running a scanning application.

The three-dimensional dataset is determined, in particular contact-free, using a 3D-scan device scanning the limb. In the state of the art, such 3D scanning devices for measuring a person or parts of a person, in this case the limb, in particular in a high precision, have already been proposed. In particular, if a contact-free 3D scan device, for example an imaging-based device, is used, the whole procedure of measuring the limb becomes contact-free. If also a tension value required as a production value is automatically determined, no tension or force needs to be exerted onto the skin of the person. In summary, a highly comfortable and reliable way of measuring the production values required for producing the compression garment is provided, in particular opposed to the traditional, unreliable way of measuring the limb using a measuring tape.

In particular, a tablet or mobile phone running a scanning application computer program may be used as the 3D scan device. Tablets or mobile phones usually comprise an optical imaging sensor, in particular a camera, and/or position and/or acceleration sensors, the latter in particular allowing to derive a position information associated with images taken by the camera. Application computer programs ("apps") have been developed which evaluate images of a limb taken from different positions, in particular orientations with respect to the limb, such that the contour/surface of the limb can be determined in three dimensions. In such an advantageous embodiment of the current invention, staff at a medical store only needs a tablet or mobile phone to determine all production values relevant for producing a compression garment, for example the skin value and the tension value at multiple measurement positions. No contact to the limb is required.

It should be noted at this point that a 3D scan device, in particular the application computer program, may also be configured to evaluate the three dimensional dataset and/or to determine the measurement positions and/or the production value itself, and/or to send the three-dimensional dataset or any self-derived results to another computing device, in particular of a determination system, where the production values may be finally determined. In particular, the computing device of the determination system may be or comprise at least one server of a manufacturer of compression garments, where also the rule set may be stored and/or the compression garment for the limb is automatically produced according to the determined production values. The 3D scan device may then use the internet to send the three-dimensional dataset, intermediate results, determined production values and/or further information.

As already mentioned, the evaluation of the three-dimensional dataset may comprise determining a surface of the limb. Since a compression garment is supposed to abut to this surface, relevant production values, for example the skin value as the circumference of the limb, may be determined from corresponding information. For example, the surface as a result of the evaluation may be described using a mesh.

In preferred embodiments, at least one reference information may be determined by analyzing the sequence of at least one characterizing value of the limb along the limb, wherein the characterizing value is determined from the three-dimensional dataset. For example, the characterizing value may comprise at least one diameter and/or a circumference of the limb and/or at least one dimension of at least one anatomical feature, in particular anatomical structure and/or landmark. Measurement positions may also be defined by relative dimensions of the limb and/or anatomical structures. For example, if a leg including the foot is measured as the limb, a measurement position may be defined as or depending on the location of the broadest extent of the foot and/or the smallest extent above the malleolus and the like. Preferably, therefore, analyzing the sequence comprises finding a local and/or global maximum or minimum of the characterizing value along the length of the limb. In embodiments, also a functional relationship between the length of the limb and the characterizing value may be derived and analyzed, for example as a curve.

At least one reference information may describe the position of an anatomical landmark, in particular a joint and/or a bone and/or a muscle and/or a tendon. For example, if the limb is a leg, a reference information may describe the position of the malleolus and/or toe joints and/or the patella and/or a center point of a muscle and/or a tendon.

Preferably, at least one rule may define a measurement position depending on at least one position of an anatomical feature of at least one reference information. In some cases, the position of the anatomical feature may already be the measurement position to be defined, in other cases, the measurement position may be calculated or otherwise derived from the position of the anatomical feature. For example, a measurement position may be defined as a certain distance above and/or below the position of the anatomical feature, for example as 2 cm below the edge of the patella or the like. However, more complex calculations may also be performed, for example positions in the middle or at certain percentage of a distance between two positions of anatomical features.

It is noted that rules of the rule set may also define decision trees, that is, contain logical operators and the like. For example, a measurement position may relate to reference information as, for example, the position of a local maximum of a characterizing value as discussed above, but at least a certain distance to a position of an anatomical feature. For example, a measurement position may be defined as the narrowest location of the trunk, but at least 10 cm above a certain anatomical feature of the hip joint.

In an especially preferred embodiment, for at least one measurement position, at least two rules for determining the measuring position using at least two different and available reference informations are provided in a rule set and all rules are used for a possibility check or for statistically refining the associated measurement position. Regarding some suitable measurement positions, they may, for example, be defined relatively to different anatomical features or regarding different characterizing values. For example, a position on the lower leg may be defined as being a certain distance above the malleolus or as being a certain distance above the bottom side of the foot. As usually the evaluation regarding different anatomical features may in many cases be relatively independent, it can, for example, be checked whether both rules provide the same result and/or a better estimation of the measurement position may be provided by statistically combining the results of two or more rules. Another example may be a measurement position that can, on the one hand, be related to the position where a circumference is largest, on the other hand as, for example, be defined as a certain percentage of the distance of two anatomical features away from one of these anatomical features. As these examples show, a redundancy regarding at least some rules may be artificially provided to allow for plausibility checks regarding the evaluation and/or to provide higher quality results for measurement positions.

According to the invention, it may also be provided that, for each reference information, at least one confidence information is determined, wherein a confidence value derived from the confidence information is associated with each measurement position and/or production value. Often, evaluation algorithms provide confidence information, describing the confidence that may be placed in their result. Such confidence information may be propagated, in particular according to the rules, to determine a confidence value for measurement positions and/or production values. This may, in particular, also be used regarding plausibility checks and/or a statistical combination of results of the different rules, for example, when calculating weights.

In especially preferred embodiments, a skin value, describing the circumference of the limb without any applied compression, is determined as at least one of the at least one production value at the at least one associated measurement position. The skin value, as already discussed in the introduction, is an often-used production value and may easily be derived from the three-dimensional dataset automatically, once the measurement position along the length of the limb is known.

Advantageously, as an additional production value, a tension value describing the circumference of the limb with the compression garment applying a desired compression may be calculated from the skin value according to a calculation instruction parameterized by at least one parameter, the parameter being derived from a dataset comprising multiple associated tuples of skin values and tension values.

According to such an embodiment, the skin value of the limb is automatically determined at at least one automatically determined measurement position and the tension value of the limb is calculated from the skin value according to a calculation instruction parametrized by at least one parameter, the parameter being predetermined and fixed, or being derived from a tuple dataset comprising multiple associated tuples of skin values and tension values.

By analyzing data on skin value and tension value, it has been surprisingly discovered that there is a correlation between skin value and tension value suitable for calculating the tension value from the skin value. This allows only performing the (well-defined) measurement regarding the skin value, in this case by using a 3D scan device, as discussed above. The calculation instruction is then used to calculate the tension value from the skin value. The calculation instruction is parametrized by at least one parameter, which may be fixed, or, preferably, be determined by evaluating known data on skin measurements and associated tension values. The calculation instruction thus describes the correlation between the skin value and the tension value, for example according to a mathematical function whose coefficients, that is, the at least one parameter, is determined in a fitting process.

In this context, the higher the number of data points, that is, tuples, in the tuple dataset, the better can the correlation between skin value and tension value be described. In this respect, it is particularly advantageous to use so-called big data evaluation to determine the parameter. In concrete embodiments, the tuple dataset may comprise at least 1,000 different tuples, in particular at least 100,000 different tuples.

By using a calculation instruction to calculate the tension value of the limb from the skin value of the limb, a standardized, consistent, unified and reproducible method for determining the tension value is provided. Since, preferably, the tuples in the tuple dataset relate to actually produced compression garments, a reliable foundation is provided and realistic correlations are derived.

In most cases, the skin value and the tension value will be required at different measurement positions along the length of the limb. That is, generally, at least one measurement position will be associated with each pair of skin value and tension value.

In a preferred, simply realizable embodiment, the parameter may be a factor with which the skin value of the limb is multiplied. Of course, the factor may also be used to perform a division. In this manner, a simple calculation instruction is provided, in particular as tension value=factor*skin value. Other or extended calculation instructions, for example comprising addition or subtraction, are also conceivable.

In an especially preferred embodiment, at least one input classification information, each relating to an information class, is provided with the three-dimensional dataset and/or derived from the three-dimensional data set, wherein the at least one parameter is chosen depending on the input classification information and/or as a parameter associated with the input classification information. The input classification information allows a refinement regarding the correlations, since the concrete parameters may also depend on such additional information, for example gender, such that, in this example, different parameters apply for male and female persons. To derive parameter values for different classification information relating to an information class, preferably each tuple of the tuple dataset additionally comprises, for each information class, a dataset classification information associated with its skin value and tension value, wherein the parameter is determined from at least one subset of the dataset tuples comprising at least one dataset classification information matching the corresponding input classification information and/or by interpolation regarding at least one of the at least one input classification information. That is, the tuple dataset can be organized into subsets relating to certain classification information of certain information classes. In the above-mentioned example of the gender of the person, for example, there may be a subset containing tuples for male persons and a subset containing tuples for female persons. However, usually, multiple information classes will be used, such that subdivisions for each information class and/or subdivisions regarding groups of information classes may be performed, yielding, for example, subsets regarding females of one age group and another subset regarding males of another age group and so on.

In particular, regarding the use of multiple information classes, different approaches may be taken to derive parameters depending on the correspondingly provided input classification information, which can also be used complementary.

In a first approach, subparameters may be determined for at least two subsets relating to different information classes, wherein the parameter is determined by using an, in particular weighted, mean of the subparameters. In this embodiment, subsets for groups of information classes and/or, preferably, single information classes, are defined to form subsets dividing the whole tuple dataset according to different classification information of the respective information class or information classes. For example, regarding the gender of the person, the tuple dataset may be subdivided into the first subset regarding male persons and a second subset regarding female persons. The same can be done for other single information classes or groups of information classes. For example, if a second information class concerns the age of the person, subsets for different age categories, that is, intervals of the age as classification information, may be formed. If, now, the input classification information relates to a person of certain gender and certain age category, subparameters may be derived from the subsets relating to the same input classification information. A parameter may be determined by taking the mean of the two subparameters, or, preferably, the weighted mean, such that, for example, gender has a higher weight than age or vice versa. Generally, more than two subparameters may be determined and, in particular, respectively weighted. This approach thus adds a lot of flexibility regarding the influence of certain input classification information. In particular, the weights themselves may be determined from the tuple dataset, in particular by evaluating the differences of subparameters derived from the subsets for different values of the classification information for each information class.

In another embodiment, which may also be used in combination with the first embodiment, the parameter or at least one subparameter may be determined from a subset for which at least two input classification informations match the corresponding dataset classification information. In this approach, the intersections between subsets regarding a single information class are determined as the relevant subset, from which the parameter or at least one subparameter is determined. For example, if a gender of the person is used as an information class and the age group is used as another information class, the relevant subset may only contain the persons of the gender and age group provided as input classification information. This may lead to a higher quality approximation of the parameter, but requires larger numbers of tuples.

In concrete embodiments, the at least one information class may be chosen from a group comprising a country class describing a country where the compression garment is to be used, a compression class, a garment information class, an indication class containing medical indications to be treated using the compression garment, a measurement position class comprising measurement positions along the length of the limbs, a limb class, a person age class, a person weight class, a person gender class, a compression garment length class, and a person tissue property class.

It can be shown that, in different countries, different requirements or desires regarding the wearing comfort of the compression garment exist, such that a country class may be used as an information class. For example, when evaluating the tuple dataset, different parameters may result for different countries.

Compression classes of compression garments are already known in the state of the art and provide information regarding the desired compression to be applied to the limb. This, in turn, may lead to different tension values to achieve the desired compression level. For example, mild compression may relate to compression values in the interval of 18 to 21 mmHg, moderate compression may be associated with the compression interval of 23 to 32 mmHg, and so on.

Regarding the possible garment information class, garment classification information may, for example, describe the type of the compression garment, and/or concrete properties, in particular an elasticity along at least one knitting direction and/or a wall stability of the compression garment. These compression garment properties may also influence the determination of tension values from skin values.

An indication class containing medical indications to be treated using the compression garment may describe what the aim of the treatment using the compression garment is, providing certain hints on the desired compression and/or other properties of the compression garment.

Regarding the measurement position class, measurement position classification information items may preferably be defined according rule set, for example using guidelines like RAL-GZ 387/1 relating to compression stockings. For example, in case of a leg, certain predefined measurement positions along the leg may be determined from the three-dimensional dataset and used to determine skin values and tension values for each of these positions to be able to produce a suitable compression garment, for example compression stocking.

In a limb class, limb classification information items may, for example, comprise a leg, an arm, or even finer distinctions, for example lower leg, upper leg, knee, foot and the like. In a patient age class, patient age classification information may be a certain age or a certain age group/category. The same may be true for a person weight class, while a person gender class, as already explained above, usually has only two classification information items, namely (biologically) male and female.

Regarding the compression garment length class, a compression garment length classification information may describe the at least one measurement position where the garment ends, such that different compression properties/different desired compressions may be associated with this measurement position along the length of the limb, depending on whether the garment ends there or not. Usually, a compression garment provides less compression at the end positions. For example, compression stockings having different lengths are known in the state of the art, as well as compression wraps and/or compression bandages. It is, for example, possible, that a compression stocking ends at the knee or that it extends further to the upper legs.

Regarding the patient tissue property class, certain tissue properties may be described which may influence the tension value at the desired compression. Preferably, the tissue properties may be measured, that is, an input classification information of the patient tissue property class may be determined by measurement, in particular also by evaluation of the three-dimensional dataset or at least one further dataset, or by using dedicated measurement devices. For example, hardness testers or the like may be used.

It should be noted that it is also possible to provide at least one additional parametrizing information which is used as or for determination of at least one of the at least one parameter. In particular in cases, in which a relationship of the parameter to the additional parametrizing information is known theoretically and/or from other sources, in may be directly applied.

Each tuple of the tuple dataset additionally comprises a reliability information associated with its skin value and tension value, wherein, when deriving the parameter from the tuple dataset, tuples are excluded and/or weighted according to their reliability information. In particularly advantageous embodiments, the reliability information comprises information regarding complaints received relating to a compression garment produced using the skin value and the tension value of the tuple. In this manner, tuples relating to actually produced garments in which there has been a complaint, in particular regarding the fitting, may be excluded from deriving the parameter or at least lowly weighted, since the combination of skin value and tension value did not lead to satisfaction or contentment of the person for which the garment was produced. In this manner, suboptimally measured or even erroneous measurements may be excluded or have their impact reduced. Of course, also other reliability information may be used, for example, a confidence level entered by a person making measurements and/or an automatically deduced confidence information, for example depending on a known skill level/experience of a person taking the measurement underlying the tuple. If, as is preferred, the tuple dataset is augmented by tuples being determined according to the current invention, a reliability information may also be determined based on the derivation of the parameter and/or the calculation of the tension value of the limb from the skin value of the limb. Known techniques and mathematical methods may be used to trace/keep track of possible errors, for example, the calculation of the standard deviation when determining the parameter from a tuple dataset or at least one subset.

As already noted, preferably, new tuples, wherein the tension value has been calculated according to the invention, may preferably be added to the tuple dataset. In an especially preferred embodiment, however, the skin value and the tension value of the limb are added as new tuples to the database only as soon as reliability information regarding these values becomes available. For example, if a compression garment is produced for the person, the corresponding tuple of skin value and tension value is not added to the tuple dataset before feedback from the person for whom the compression garment has been produced if received. In this manner, the reliability information, in particular regarding the fitting of the compression garment, is already available when the new entry to the tuple dataset is added and/or the addition of the tuple may be omitted if the reliability information indicates a low quality.

In preferred embodiments, at least one length value describing the distance between two measurement positions along the limb is determined as at least one of the at least one production value. Such length values, in German also called "Längsmaß", may convey information regarding the extension of the limb which may also be relevant regarding the production of the compression garment. It is, in particular, noted, that the measurement positions themselves, in any case, form additional production values, which may be understood as length values, since they are provided with production values determined at the respective measurement positions and consequently provided with these determined production values anyway, used during production of the compression garment.

Preferably, if the compression garment is to be produced by flat knitting, the length value is determined along the outline of the limb and, if the garment is to be produced by circular knitting, the length value is determined along a longitudinal axis of at least a part of the limb. That is, depending on the knitting method, different suitable ways of determining length values may be used. In the case of flat knitting, the length value is determined using the contour of the limb, while in the case of circular knitting, a longitudinal axis of the limb is used as a reference, in particular by letting fall a perpendicular.

The rule set may be fixed, however, in a preferred embodiment, the rule set is updated using machine learning and training data obtained from actually produced garments. That is, for example, feedback regarding the compression garment, once produced, may be used to adapt the rules if it becomes known that the measurement position could have been determined more precisely. Machine learning techniques, for example employing artificial intelligence algorithms like neural networks, may be employed. In especially advantageous embodiments, the database used for determining the parameter, as defined above, may be expanded to also contain training data for updating the rule set in each tuple.

It is noted that rules may also be defined by using other rules, of course, which may be inserted if the other rule should not be applied. For example, a first rule may define a first measurement position, wherein a second rule may define a second measurement position dependent on the first measurement position, such that, to solely find the second measurement position directly from the reference information, the second rule includes application of the first rule.

A concrete, advantageous rule set for a leg as a limb may comprise the following rules for measurement positions:
- a first measurement position may be determined as 2-4 cm, in particular 3 cm, above the malleolus;
- the first measurement position may also be determined as 8-12 cm, in particular 10 cm, above the bottom side of the foot;
- a second measurement position may be determined as 1.5 to 2.5 cm, in particular 2 cm, below the lower edge of the patella and/or 4 to 6 cm, in particular 5 cm, below the middle of the patella;
- a third measurement position may be defined as two thirds of the distance between the first measurement position and the second measurement position above the first measurement position;
- a fourth measurement position may be defined as one third of the distance between the first measurement position and the second measurement position above the first measurement position for flat knitting and/or as one half of the distance between the first and the third measurement position above the first measurement position for circular knitting;
- a fifth measurement position may be defined as 2-4 cm, in particular 3 cm, below the crotch and/or as the largest diameter area of the upper leg;
- a sixth measurement position may be defined as one half the distance between the middle of the patella and the fifth measurement position; and
- a seventh measurement position may be defined as the position of the smallest circumference of the trunk, but at least 13-17 cm, in particular 15 cm, above the position of largest circumference of the buttocks.

In particular in cases where ranges are mentioned in these exemplary rules, it is preferred to use the above-mentioned machine learning to further refine these rules over time.

The invention also concerns a method for producing a compression garment for a limb of a person, comprising automatically performing the steps of a method for determining a production value as described above, whereafter the compression garment is automatically produced by a garment production apparatus, in particular a knitting machine, using the production value. In particular, a computing device of a manufacturer may thus receive, in particular along with input classification information, the three-dimensional dataset and/or intermediate evaluation results and/or at least one of the at least one production value, the three-dimensional dataset being, for example, measured in a medical store. Automatically, the at least one production value is determined, in particular the skin value and additionally a tension value at different measurement position. At this time, all information for automatically producing the custom-tailored compression garment for the limb of the person is available at the computing device of the manufacturer, such that the garment production apparatus, in particular a knitting machine, can be controlled to correspondingly produce the custom-tailored compression garment for the limb of the person. Thus, a fully automatic, reliable and simply implementable way of producing custom-tailored compression garments is provided.

As already noted, different types of compression garments may be produced according to the invention, for example compression stockings, compression bandages and/or compression wraps.

The invention also concerns a determination system for at least one production value for producing a custom-tailored compression garment for a limb, wherein the production value is associated with at least one measurement position along the length of the limb, comprising:
- an interface for receiving a three-dimensional dataset of the limb acquired using a 3D scan device,
- an evaluation unit for evaluating the three-dimensional dataset to derive at least one reference information describing the position of an anatomical feature of the limb along the length of the limb,
- a first determination unit determining the at least one measurement position for the at least one production value in the three-dimensional dataset using at least one rule of a rule set, wherein each rule relates at least one reference information to at least one measurement position,
- a second determination unit for determining the at least one production value from the three-dimensional dataset at the at least one determined measurement position, and
- a storage means wherein the rule set is stored.

In other words, the determination system is configured to perform a method according to the current invention. All features and comments regarding the method according to the invention correspondingly apply to the determination system according to the invention.

The determination system may comprise one or more computing devices, in particular being or comprising at least one server. For example, a three-dimensional dataset measured in a medical store may be communicated, using the internet or another communication connection, to the interface, which is a part of at least one of the at least one computing device, in particular of a server. Here, the determination of the at least one production value may take place. The rule set may be stored in the same computing device, in particular server, as may, if used, be the tuple dataset. It is, however, also possible that the rule set and/or the tuple dataset is stored in the storage means of another computing device, in particular server. In preferred embodiments, if a tablet and/or a mobile phone, as discussed above, acts as 3D scanning device for measuring the skin value, the corresponding computer application program/the tablet or mobile phone may already be configured to send the three-dimensional dataset and/or intermediate results, ins particular the reference information, to the at least one computing device of the determination system, in particular the interface. It is, however, also possible to perform at least a part of the steps in the tablet or mobile phone. In any case, the tablet or mobile phone may form part of the determination system.

In embodiments, a determination system may be part of a compression garment production system, which additionally comprises a garment production apparatus and an associated controller, wherein the controller controls the garment production apparatus to produce a compression garment using the determined production values. To this end, a knitting program may be determined in the determination system, for example in a computing device and/or using the controller.

It is noted that a processor according to the current invention is to be understood as any device that is able to process data. For example, the processor may be or comprise at least one CPU and/or GPU and/or integrated circuit and/or FPGA or the like. By the processor, certain functional units may be realized, for example units as named above.

A computer program according to the invention can, for example, be directly loaded into a storage means of a computing device, in particular the determination system, and comprises program means to perform the steps of a method according to the invention when the program is executed in the computing device. The computer program may be stored on an electronically readable storage medium, which thus comprises electronically readable control information stored thereon, which in turn comprises at least the computer program according to the invention and is configured such that, when the storage medium is used in a computing device, in particular a determination system, the steps of a method according to the invention are performed. The electronically readable storage medium may be a non-transitional storage medium, for example a CD-ROM.

Figure 2:
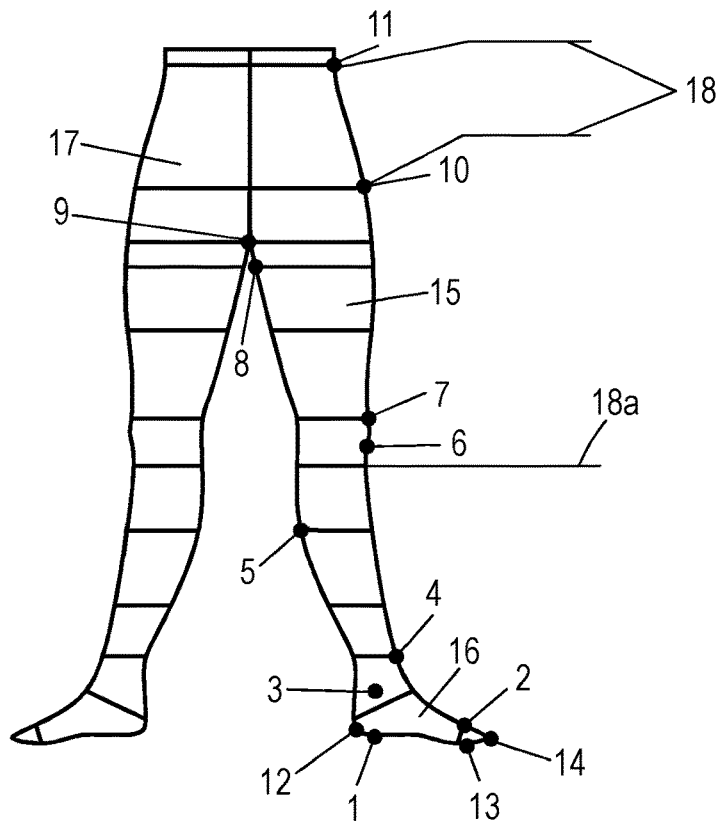

Further details and advantages of the current invention may be taken from the following description of preferred embodiments taken in conjunction with the drawings, in which:

FIG. 1 is a flowchart of an embodiment of a method according to the invention, FIG. 2 shows limbs of a person, and FIG. 3 shows an embodiment of a determination system according to the invention.

The flowchart of FIG. 1 illustrates an embodiment of a method according to the invention. The aim of the method described in the following is to produce a custom-tailored compression garment for the limb of a person. In a step S1, a three-dimensional dataset of the limb is acquired, for example by staff of a medical store.

The three-dimensional dataset is measured using a 3D scan device, which may in particular be realized as a tablet or mobile phone, on which an application computer program is provided. For example, a camera of the tablet or mobile phone may be used to image the limb from multiple views, which may be evaluated to derive a three-dimensional surface representation and thus the three-dimensional dataset. Alternatively to such a tablet or mobile phone, the 3D scan device may be a dedicated scanner, for example a whole-body scanner and/or a limb scanner. The use of a 3D scan device is advantageous, since a contact-free measurement is possible and the measurement is not confined to only a few measurement positions.

In a generally optional step S2, additional information regarding the person, in particular a patient, and/or the garment is gathered as input classification information for, in this case, multiple information classes. The information classes may comprise a country class describing a country where the compression garment is to be used, a compression class, a garment information class, an indication class containing medical indications to be treated using the compression garment, a measurement position class comprising measurement positions along the length of the limb, a limb class, a person age class, a person weight class, a person gender class, a compression garment length class and/or a person tissue property class. For example, input classification information may be entered using the 3D scan device, in particular the tablet or mobile phone. In the case of patient tissue properties, these may also be measured, for example by using a hardness tester or the like. It is noted that the input classification information, which will, as described below, be used for determining a tension value as additional production value, may be complemented by results of the evaluation of the three-dimensional dataset, in particular be adding actually used measurement positions.

In a step S3, which may be performed on the 3D scan device or on a computing device, in particular a server, of a manufacturer of compression garments, the three-dimensional dataset is evaluated to derive reference information. Each reference information describes the position of at least one anatomical feature in the limb, as described in the three-dimensional dataset. These positions are, preferable, defined along the length of the limb. At least a part of the reference information is determined by analyzing how a characterizing value of the limb changes along the limb, for example a diameter or a circumference of the limb or a dimension of an anatomical structure. The characterizing value is determined from the three-dimensional dataset. For example, the sequence of characterizing values along the lengths of the limb may be analyzed to find a local or global maximum or minimum of the characterizing value along the length of the limb, for example to find a position where the limb is broadest or narrowest or the like. Other examples for reference information include the position of an anatomical landmark along the limb, for example a joint, a bone or the like.

In a step S4, a rule set, which may be stored in a storage means of the computing device and/or the 3D-scan device, is used to determine measurement positions for determining certain production values, in this case at least the skin value, from the reference information. Rules may define measurement positions depending on at least one position of an anatomical feature of at least one reference information and may also comprise conditions and/or logical operators.

For example, a measurement position may be defined as the broadest location of a foot or relatively, for example, as the narrowest location above the malleolus. Other rules may be to take a certain percentage of a distance between two anatomical features and/or use absolute distances to such an anatomical feature. Finally, definitions like a certain distance from the position of an anatomical feature, but at least 10 cm below another anatomical feature are also possible.

In this embodiment, for at least some measurement positions, two or more rules regarding the determination exist in the rule set. For example, a measurement position may relate to an anatomical feature as being a certain distance away, but also to another anatomical feature, for example as corresponding to the position of this other anatomical feature. In this case, a plausibility check may be performed if both reference informations are available. Additionally or complementary, both results of application of the rule may be statistically combined.

In a step S5, the production values are determined at (or in some cases even as) the measurement positions. In this embodiment, in the step S5, at least a skin value is determined at each measurement position. The skin value is defined as the circumference of the limb at the measurement position with no tension force exerted onto the skin. Thus, it may be easily derived from the three-dimensional dataset.

FIG. 2 shows an example of anatomical features and their positions 1-14 in a hip- and leg-area of a person, that is, legs 15 with corresponding feet 16 as well as the hip area 17 is shown. The lines 18 each mark measurement positions along the limb. The shown anatomical features, in this case, are as follows:

| reference position | anatomical feature |
| --- | --- |
| 1 | bottom side of foot |
| 2 | broadest location of the foot |
| 3 | malleolus |
| 4 | narrowest location above malleolus |
| 5 | largest circumference of lower leg |
| 6 | lower edge of patella |
| 7 | middle of patella (popliteal cavity) |
| 8 | largest circumference leg |
| 9 | crotch |
| 10 | largest circumference buttocks |
| 11 | smallest circumference trunk |
| 12 | end of heel |

-continued

| reference position | anatomical feature |
|---|---|
| 13 | metatarsophalangeal joint of the big toe |
| 14 | tip toe |

In this example, the measurement position indicated by line 18a may, for example, be determined using a rule "2 cm below the edge of the patella (position 6)" and/or "5 cm below the middle of the patella (position 7)".

In a step S6, for each measurement position, a calculation instruction is used to calculate a tension value of the limb from the skin value of the limb using a calculation instruction, in this case by multiplying the skin value with a factor. The factor is thus a parameter of the calculation instruction. In this embodiment, the parameter is determined depending on input classification information.

In a storage means, which may also store the rule set, a tuple dataset comprising tuples of skin values and associated tension values, as well as dataset classification information associated with the pair of skin value and tension value, is stored. The maintenance of this tuple dataset is indicated by a step S7 and takes place continuously.

In particular, all tuples present in the tuple dataset relate to actually produced compression garments, such that a reliability information is also associated with each tuple. In this embodiment, the reliability information at least describes whether there has been a complaint regarding the fitting of the compression garment. New tuples, in this respect, as only added to the tuple dataset once the respective reliability information becomes available. In particular, feedback regarding produced compression garments is awaited before a tuple is eligible for entry into the tuple dataset.

In a step S8, a parameter to be used in step S6 is derived from the tuple dataset also using the input classification information. Two examples for the case of multiple information classes used shall be discussed as examples here.

In a first concrete example, for each information class, subsets are derived from the tuple dataset, wherein a subset for each information class is generated by selecting all tuples in which the input classification information of the information class equals the dataset classification information of the respective tuple. For example, if the information class is a person gender class, and the input classification information is "female", a respective subset contains all tuples that relate to female persons.

For each subset generated in this manner, a subparameter is derived, for example, by fitting the calculation instruction to the tuples in the subset. In this process, tuples for which the reliability information shows a complaint regarding fitting may be excluded or lower weighted.

From the subparameters for all information classes, the parameter is derived by calculating the mean, in particular a weighted mean, such that the impact of certain information classes may be taken into account.

In a second example, only one subset is generated from the tuple dataset, the subset containing all tuples for which all input classification information match the respective dataset classification information. The subset is thus an intersection of all the subsets generated in the first example. From this subset, the parameter is, again, derived by fitting the calculation instruction to the tuples.

It should be noted that is of course also possible to combine the first example and the second example, for example by forming subsets for groups of information classes instead of only single classes. If a classification information includes a continuous value, it is also possible to derive, in particular by interpolation, a function which describes how the parameter depends on the respective classification information. For the respective information class, the parameter or subparameter may thus be calculated.

The parameter derived from the tuple dataset depending on the input classification information in step S8 is then used in step S6 to calculate the tension value.

In a step S9, the measurement positions, their associated skin values and calculated tension values, optionally further production values and the input classification information, at least in part, are used to produce a custom-tailored compression garment for a person. As has already been noted, feedback regarding the fitting may be awaited before entering the newly calculated tuple into the tuple dataset.

FIG. 3 illustrates an exemplary determination system 19 for performing the method according to FIG. 1. In this case, the determination system 19 also comprises the 3D scan device 20, in particular a tablet 21, whose camera 22 may be used to accordingly scan the limb 23 of a person. The tablet 21 may also be used to gather and assemble at least a part of the input classification information.

The measured three-dimensional dataset is sent to a computing device 24 of the manufacturer of compression garments through the internet 25 and/or mobile networks. The three-dimensional dataset of the limb 23 and the input classification information are received by an interface 26. The computing device 24, which may be a server, in this case also comprises at least one processor 27 for performing the evaluations, determinations and calculations in steps S3, S4, S5, S6 and S8. It is noted that the processor 27 may, at least in part, also be realized distributedly, for example regarding other computing devices 28 of the manufacturer, in particular other servers. In this example, the tuple dataset 29 is stored in a storage means 30 of a second computing device 28, as is the rule set 34. The storage means 30 and thus the tuple dataset 29 and the rule set 34 may be accessed by the processor 27.

The production values (for each measurement position) and the input classification information are then transferred to a garment production apparatus 31, in this case a knitting machine 32, where they are used by a controller 33 to produce the custom-tailored compression garment for the limb 23 of the person. In particular, a knitting program may be derived from the production values. Alternatively, a knitting program may be compiled on a computing device 24, 28, according to these informations, and be transferred to the garment production apparatus 31.

It is noted that in some embodiments, the determination system 19 may only comprise the at least one computing device 24, 28. If the garment production apparatus is added, the determination system 19 may also be understood as garment production system.

The invention claimed is:

1. Computer-implemented method for determining at least one production value for producing a custom tailored compression garment for a limb (23), comprising the steps of:
receiving a three dimensional dataset of the limb (23) acquired using a 3D scan device (20),
evaluating the dataset to derive at least one reference information describing the position (1-14) of an anatomical feature of the limb (23) along the length of the limb (23),
determining the at least one measurement position for the at least one production value in the three dimensional dataset using at least one rule of a rule set (34), wherein each rule relates at least one reference information to at least one measurement position, and determining the at least one production value from the three dimensional dataset at the at least one determined measurement position, wherein the production value is associated with at least one measurement position along the length of the limb (23), wherein a skin value, describing the circumference of the limb (23) without any applied compression, is determined as at least one of the at least one production value at the at least one associated measurement position, and wherein, as an additional production value, a tension value describing the circumference of the limb (23) with the compression garment applying a desired compression is calculated from the skin value according to a calculation instruction parametrized by at least one parameter, the parameter being predetermined and fixed, or being derived from a tuple dataset (29) comprising multiple associated tuples of skin values and tension values.

2. Method according to claim 1, characterized in that the three dimensional dataset is acquired using a contact-free, imaging-based 3D scan device (20), in particular a tablet (21) or mobile phone running a scanning application.

3. Method according to claim 1, wherein the evaluation of the three dimensional dataset comprises determining a surface of the limb (23).

4. Method according to claim 1, wherein at least one reference information is determined by analyzing the sequence of at least one characterizing value of the limb (23) along the limb (23), wherein the characterizing value is determined from the three-dimensional dataset.

5. Method according to claim 4, wherein analyzing the sequence comprises finding a local and/or global maximum or minimum of the characterizing value along the length of the limb (23).

6. Method according to claim 1, wherein at least one reference information describes the position (1-14) of an anatomical landmark, in particular a joint and/or a bone and/or a muscle and/or a tendon.

7. Method according to claim 1, wherein at least one rule defines a measurement position depending on at least one position (1-14) of an anatomical feature of at least one reference information.

8. Method according to claim 1, wherein, for at least one measurement position, at least two rules for determining the measurement position using at least two different and available reference information are provided in the rule set (34) and all rules are used for a plausibility check or for statistically refining the associated measurement position.

9. Method according to claim 1, wherein at least one length value describing the distance between two measurement positions along the limb (23) is determined as at least one of the at least one production value, wherein in particular, if the compression garment is to be produced by flat knitting, the length value is determined along the outline of the limb (23) and, if the garment is to be produced by circular knitting, the length value is determined along a longitudinal axis of at least a part of the limb (23).

10. Method according to claim 1, wherein the rule set (34) is updated using machine learning and training data obtained from actually produced compression garments.

11. Method for producing a compression garment for a limb (23) of a patient, comprising automatically performing the steps of a method according to claim 1, whereafter the compression garment is automatically produced by a garment production apparatus (31), in particular a knitting machine (32), using the at least one production value.

12. Computer program, which performs the steps of a method according to claim 1 when the computer program is executed on a computing device (24, 28), in particular of a determination system (19).

13. Determination system (19) for at least one production value for producing a custom tailored compression garment for a limb (23), wherein the at least one production value is associated with at least one measurement position along the length of the limb (23), comprising:

an interface for receiving a three dimensional dataset of the limb (23) acquired using a 3D scan device (20), an evaluation unit for evaluating the dataset to derive at least one reference information describing the position of an anatomical feature of the limb (23) along the length of the limb (23), a first determination unit determining the at least one measurement position for the at least one production value in the three dimensional dataset using at least one rule of a rule set (34), wherein each rule relates at least one reference information to at least one measurement position, a second determination unit for determining the at least one production value from the three dimensional dataset at the at least one determined measurement position, wherein a skin value, describing the circumference of the limb (23) without any applied compression, is determined as at least one of the at least one production value at the at least one associated measurement position, and wherein, as an additional production value, a tension value describing the circumference of the limb (23) with the compression garment applying a desired compression is calculated from the skin value according to a calculation instruction parametrized by at least one parameter, the parameter being predetermined and fixed, or being derived from a tuple dataset (29) comprising multiple associated tuples of skin values and tension values, and a storage means (20) wherein the rule set (34) is stored.

* * * * *